US010531797B2

(12) United States Patent
Knickerbocker et al.

(10) Patent No.: US 10,531,797 B2
(45) Date of Patent: Jan. 14, 2020

(54) WEARABLE BLOOD PRESSURE MONITORING SYSTEM

(71) Applicant: International Business Machines Corporation, Armonk, NY (US)

(72) Inventors: John U. Knickerbocker, Monroe, NY (US); Hyung-Min Lee, Elmsford, NY (US); Kang-Wook Lee, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/269,040

(22) Filed: Sep. 19, 2016

(65) Prior Publication Data
US 2018/0078153 A1 Mar. 22, 2018

(51) Int. Cl.
*A61B 5/021* (2006.01)
*A61B 5/00* (2006.01)
(Continued)

(52) U.S. Cl.
CPC .......... *A61B 5/002* (2013.01); *A61B 5/02007* (2013.01); *A61B 5/02125* (2013.01);
(Continued)

(58) Field of Classification Search
CPC .............................. A61B 5/021; A61B 5/02108
See application file for complete search history.

(56) References Cited

U.S. PATENT DOCUMENTS

| 6,432,060 | B1 * | 8/2002 | Amano | A61B 5/021 |
| | | | | 600/485 |
| 6,602,198 | B2 * | 8/2003 | Yokozeki | A61B 5/021 |
| | | | | 600/485 |
| 2014/0012146 | A1 * | 1/2014 | Fukuda | A61B 5/02108 |
| | | | | 600/485 |

FOREIGN PATENT DOCUMENTS

KR     WO 2016017930 A1 *  2/2016  ........... A61B 5/0225

OTHER PUBLICATIONS

P. Fung et al., "Continuous Noninvasive Blood Pressure Measurement by Pulse Transit Time", Proceedings of the 26th Annual International Conference of the IEEE EMBS San Francisco, CA, USA (Sep. 1-5, 2004).

(Continued)

*Primary Examiner* — Tammie K Marlen
(74) *Attorney, Agent, or Firm* — Harrington & Smith

(57) ABSTRACT

An apparatus includes one or more memories storing computer readable code and processor(s). The processor(s), in response to loading and executing the computer readable code, cause the apparatus to perform operations including receiving electrocardiogram data from an electrocardiogram sensor. The electrocardiogram data includes data from an electrocardiogram from a person. The operations also include receiving pulse wave data from one or more pulse wave pressure sensors. The pulse wave data includes data from one or more pulse waves from the person. The operations further include determining blood pressure using the electrocardiogram data or the pulse wave data from the chest (Continued)

and the pulse wave data from the wrist or finger, and outputting an indication of the blood pressure. Another apparatus uses pulse wave data from two pulse wave sensors (e.g., pulse wave pressure sensor(s) and/or PPG sensor(s)) and blood pressure determinations are made using these pulse wave data.

22 Claims, 9 Drawing Sheets

(51) Int. Cl.
  *A61B 5/02*   (2006.01)
  *A61B 5/024*   (2006.01)
  *A61B 5/0402*  (2006.01)
  *A61B 5/1455*  (2006.01)

(52) U.S. Cl.
  CPC ........ *A61B 5/02416* (2013.01); *A61B 5/0022* (2013.01); *A61B 5/0402* (2013.01); *A61B 5/14551* (2013.01); *A61B 5/681* (2013.01); *A61B 5/7282* (2013.01)

(56) References Cited

OTHER PUBLICATIONS

S. Fuke et al., "Blood pressure estimation from pulse wave velocity measured on the chest", 35th Annual International Conference of the IEEE EMBS Osaka, Japan (Jul. 3-7, 2013).
H. Gesche et al., "Continuous blood pressure measurement by using the pulse transit time: comparison to a cuff-based method", European Journal of Applied Physiology, vol. 112, Issue 1, pp. 309-315 (Jan. 2012).
S. Goli et al., "Cuffless continuous non-invasive blood pressure measurement using pulse transit time measurement", International Journal of Recent Development in Engineering and Technology, vol. 2, Issue 1 (Jan. 2014).
B. McCarthy et al., "An Investigation of Pulse Transit Time as a Non-Invasive Blood Pressure Measurement Method", Sensors & their Applications XVI, Journal of Physics: Conference Series 307 (2011).
C. Poon et al., "Cuff-less and Noninvasive Measurements of Arterial Blood Pressure by Pulse Transit Time", Proceedings of the 2005 IEEE Engineering in Medicine and Biology 27th Annual Conference Shanghai, China (Sep. 1-4, 2005).
Zhang et al., "A LabVIEW Based Measure System for Pulse Wave Transit Time", Proceedings of the 5th International Conference on Information Technology and Application in Biomedicine, in conjunction with the 2nd International Symposium & Summer School on Biomedical and Health Engineering Shenzhen, China (May 30-31, 2008).
A. Patzak et al., "Continuous blood pressure measurement using the pulse transit time; Comparison to intra-arterial measurement", Blood Pressure, 2015; Early Online: 1-5 (2015).
Y. Li et al., "Mechanism of Cuff-Less Blood Pressure Measurement Using MMSB", Engineering, 5, 123-125 (2013).
Y. Heravi et al., "A New Approach for Blood Pressure Monitoring based on ECG and PPG Signals by using Artificial Neural Networks", International Journal of Computer Applications (0975-8887), vol. 103—No. 12 (Oct. 2014).
S. Thomas at al., "BioWatch: A Non-invasive Wrist-based Blood Pressure Monitor that Incorporates Training Techniques for Posture and Subject Variability", IEEE J Biomed Health Inform. (2015).
S. Ilango et al., "A non-invasive blood pressure measurement using Android smartphones", IOSR Journal of Dental and Medical Services, vol. 13, Issue 1, Ver. IV, pp. 28-31 (Jan. 2014).
B. Kim et al., "A New Approach on Digital Blood Pressure Measurement Method for u-Healthcare Systems", International Journal of Bio-Science and Bio-Technology, vol. 7, No. 1, pp. 169-178 (2015).
Y. Yoon, JH Cho, G. Yoon, "Non-Constrained Blood Pressure Monitoring using ECG and PPG for Personal Healthcare", J Med Syst (2009) 33: 261-266.
U.S. Appl. No. 14/873,249, filed Oct. 1, 2015, our #909A.0489.
U.S. Appl. No. 14/977,855, filed Dec. 22, 2015, our #909A.0520.
D-H Nam, et al., "Measurement of Spatial Pulse Wave Velocity by Using a Clip-Type Pulsimeter Equipped with a Hall Sensor and Photoplethysmography", Sensors 2013, 13, 4714-4723.

\* cited by examiner

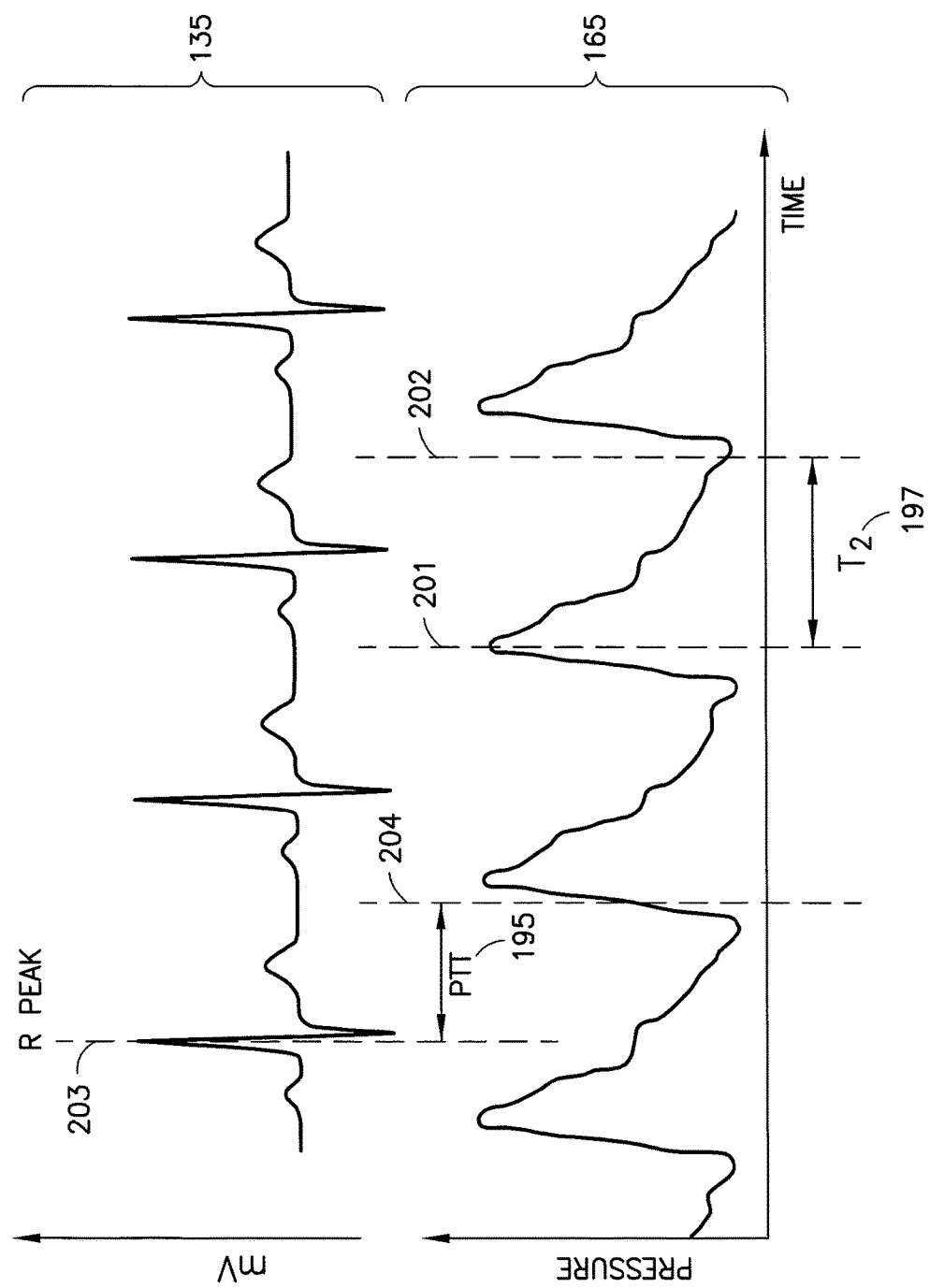

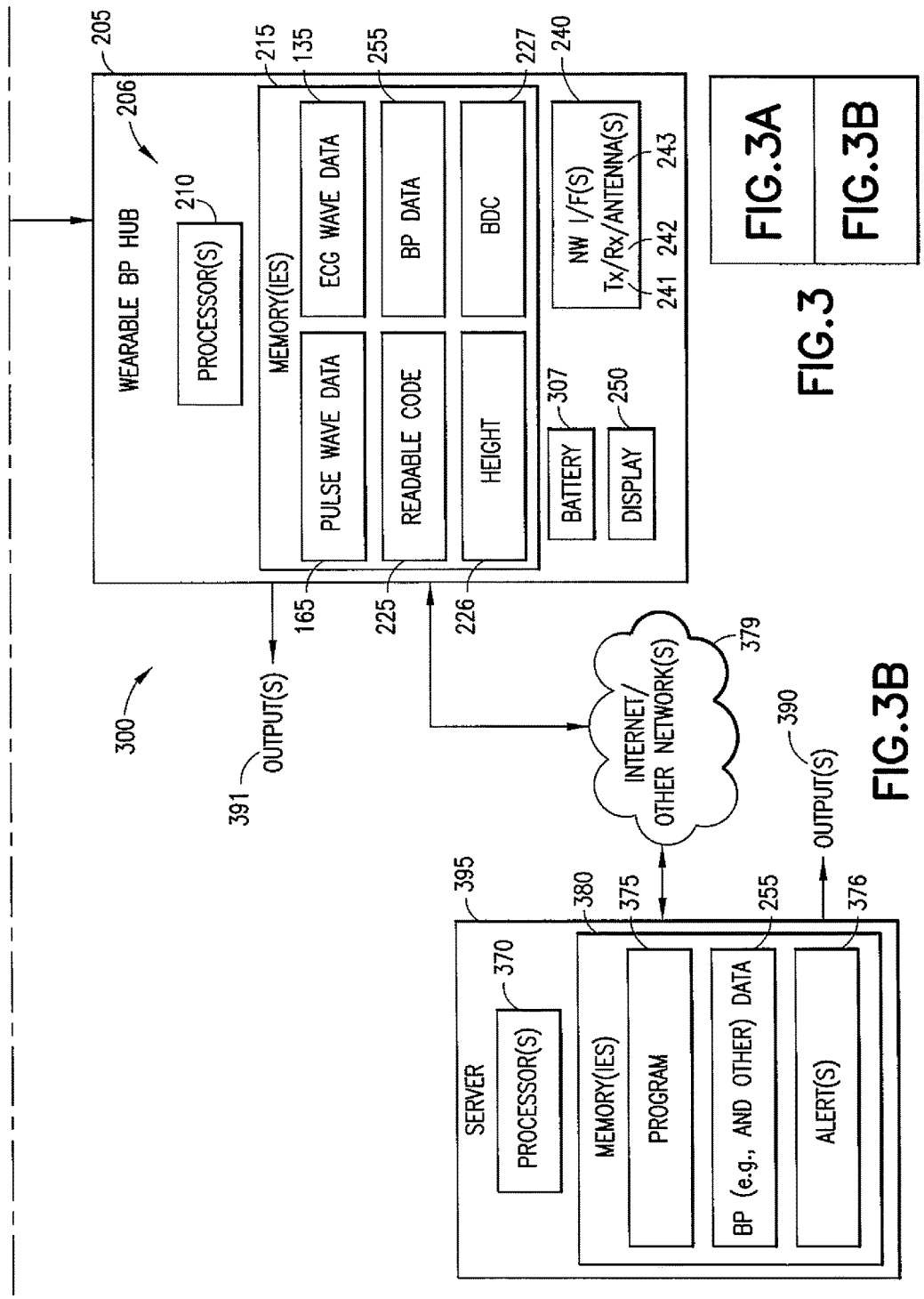

US 10,531,797 B2

WEARABLE BLOOD PRESSURE MONITORING SYSTEM

BACKGROUND

This invention relates generally to sensors and, more specifically, relates to wearable sensors.

Abbreviations used in the specification and/or drawings are defined below, prior to the claims.

Today, monitoring of personal health and wellness from detecting an early onset of a disease to monitoring recovery from medical intervention can be infrequent and/or costly. For instance, one risk factor for cardiovascular disease (CVD) is high blood pressure. Typically, high blood pressure develops over a long time period and may not be found until substantial damage has been done. Monitoring blood pressure in real time and in a remote mode could help reduce, prevent, or cure certain cardiovascular diseases.

SUMMARY

The following summary is merely intended to be exemplary. The summary is not intended to limit the scope of the claims.

In one example, an apparatus includes one or more memories storing computer readable code and one or more processors. The one or more processors, in response to loading and executing the computer readable code, causing the apparatus to perform operations comprising: receiving electrocardiogram data from an electrocardiogram sensor, the electrocardiogram data comprising data from an electrocardiogram from a person; receiving pulse wave data from at least one pulse wave pressure sensor, the pulse wave data comprising data from one or more pulse waves from the person; determining blood pressure using at least the electrocardiogram data and the pulse wave data; outputting an indication of the blood pressure.

In another example, an apparatus comprises one or more memories storing computer readable code and one or more processors. The one or more processors, in response to loading and executing the computer readable code, causing the apparatus to perform operations comprising: receiving first pulse wave data from a first pulse wave sensor placed at a first location on a person, the first pulse wave data comprising data from one or more pulse waves from the first location of the person; receiving second pulse wave data from a second pulse wave sensor placed at a second location on the person, the first and second locations being different locations on the person, the second pulse wave data comprising data from one or more pulse waves from the second location of the person; determining blood pressure using at least the first and second pulse wave data; and outputting an indication of the blood pressure.

BRIEF DESCRIPTION OF THE DRAWINGS

FIG. 2 is a graph on the same time scale of an ECG wave and a radial artery pulse wave, and illustrates determination of pulse transit time (PTT) between heart and wrist and time difference between a forward wave point and the ending point of the wave ($T_2$);

FIGS. 5A and 5B, illustrates the peripheral (radial) pressure in mmHg over time in seconds (s) for a young person (FIG. 5A) and an old person (FIG. 5B);

DETAILED DESCRIPTION

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

Figure 1:
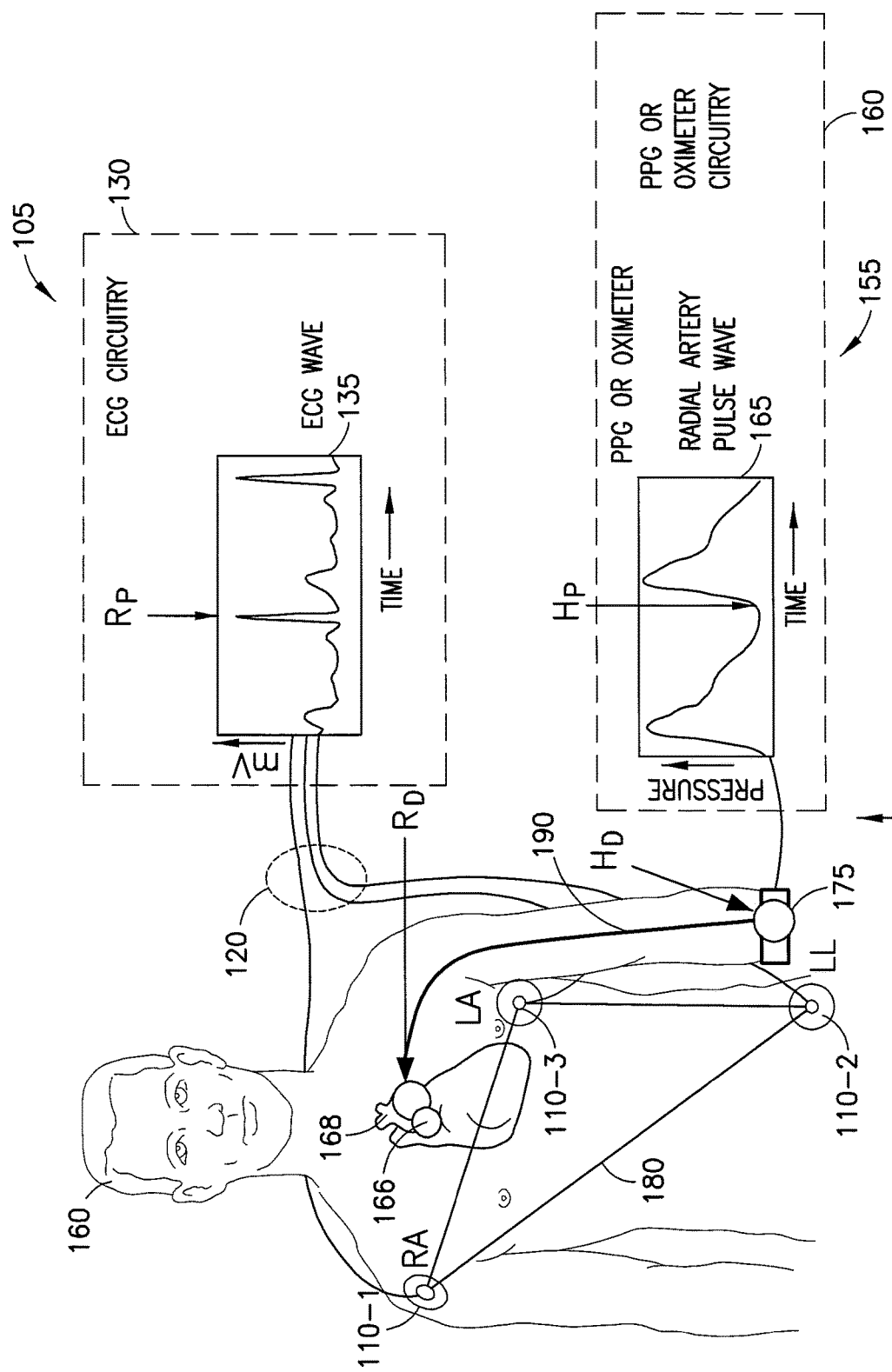
FIG. 1 illustrates a system used on a human being (i.e., a person) to determine information used for an estimate of blood pressure.

It is possible to provide an estimate of blood pressure for a human being (i.e., a person) by using data from an electrocardiogram (ECG) and at least one photoplethysmography (PPG) (also called photoplethysmogram) sensor, which is usually implemented as an oximeter. Referring to FIG. 1, this figure illustrates a system used on a human being 160 to determine information used for an estimate of blood pressure. Human being 160 is also referred to as a person herein. An ECG sensor 105 comprises ECG circuitry 130, wiring 120, and three electrodes RA 110-1, LL 110-2, and LA 110-3. The electrodes 110 are formed in a triangle 180 in this example. The ECG circuitry 130 forms ECG wave data 135 (which is data describing electrical signals from the heart 168 and is in mV, millivolts) using information from the electrodes 110. Also shown is a pulse wave sensor 155, which includes a PPG or oximeter sensor 175 and PPG or oximeter circuitry 160. The PPG or oximeter circuitry 160 creates radial artery pulse wave data 165 (based on blood flow in the artery 190) from the PPG or oximeter sensor 175. A PPG unit will determine relative blood absorbance versus time (which also indicates relative blood volume versus time). The oximeter unit determines a percentage of oxygen saturation in the artery. Here, $R_P$, $R_D$, $H_P$, and $H_D$ are the maximum R peak of ECG pulse wave, the distance of aortic valve position, the starting point of radial artery pulse wave, and the distance of radial wrist position, respectively. Also, the circle 166 and the solid line 190 are the exact position of aortic valve and the rough distance from aortic valve to wrist, respectively. This figure is from D-H Nam, et al., "Measurement of Spatial Pulse Wave Velocity by Using a Clip-Type Pulsimeter Equipped with a Hall Sensor and Photoplethysmography", Sensors 2013, 13, 4714-4723.

Turning to FIG. 2, this figure is a graph on the same time scale of an ECG wave data 135 and a radial artery pulse wave data 165. This particular exemplary radial artery pulse wave data 165 was determined using photoplethysmography (PPG) (e.g., a photoplethysmogram), however, this data may also be determined using the pressure sensors described herein. The pulse transit time (PTT) 195 may be determined by comparing the R peak 203 of the ECG wave data 135 and the corresponding maximum inclination 204 of the radial artery pulse wave data 165. See, for instance, P. Fung et al., "Continuous Noninvasive Blood Pressure Measurement by Pulse Transit Time", Proceedings of the 26th Annual International Conference of the IEEE EMBS San Francisco, Calif., USA (Sep. 1-5, 2004): "PTT in this paper is defined as the time between the ECG R peak and the corresponding maximum inclination in the PPG." The $T_2$ 197 is described below.

Using the PTT and additional information such as pulse wave velocity (PWV), height of a person, and body correlation factors, the person's blood pressure can be determined. For instance, see the P. Fung article cited above; H. Gesehe et al., "Continuous blood pressure measurement by using the pulse transit time: comparison to a cuff based method", European Journal of Applied Physiology, Volume 112, Issue 1, pp 309-315 (January 2012); and S. Fuke et al., "Blood pressure estimation from pulse wave velocity measured on the chest", 35th Annual International Conference of the IEEE EMBS Osaka, Japan (3-7 Jul., 2013).

While these are useful tools, they can be improved upon. For instance, exemplary embodiments here provide a wearable blood pressure monitoring system with a wearable ECG (electrocardiogram) on, e.g., the chest and a wearable pressure sensor on, e.g., the wrist. The wearable pressure sensor on the wrist can generate more precise artery pulse waves than a typical photoplethysmography (PPG), the technique of which is often employed for an oximeter. One of the highly sensitive pressure sensors is made of elastomeric pyramids which, upon pressing and releasing, generate pulse waves in the form of a capacitance (across the pressure sensor) versus time graph. In an exemplary embodiment, an electronic hub receives (e.g., wirelessly) ECG and pulse wave signals. Certain exemplary embodiments also include an upgraded algorithm that can provide an output of more precise blood pressures which can be transferred (e.g., wirelessly) to, for instance, a cognitive/cloud system that in turn may communicate with hospitals, doctors, and/or users.

Another possible aspect of the exemplary embodiments is to measure and store a person's artery stiffness index which is indicative of hypertension or vascular diseases. The cumulated records of blood pressures and artery stiffness indices can be used for an early diagnosis and/or cure of certain cardiovascular disease(s).

One possible aspect of the exemplary embodiment includes the use of a more wearable and sensitive pressure sensor on, e.g., the wrist. There are at least two distinct advantages of the types of pressure sensors used herein over the PPG or oximeter:

(1) A first advantage is better sensitivity to provide more precise pulse wave signals.

(2) A second advantage is much less power consumption since the pressure sensors used herein generate their capacitance variation by pulses without requiring much electrical power, while an oximeter (e.g., PPG) needs to emit light (e.g., red and infrared from LEDs) and detect reflection or transmission of the lights, which consumes a larger amount of power relative to the sensors used herein. That is, the pressure sensor still needs a little electrical power to detect capacitance variation, but this amount of power will be much smaller than the electrical power to emit light and detect light as in an oximeter (e.g., PPG).

Figure 3A:
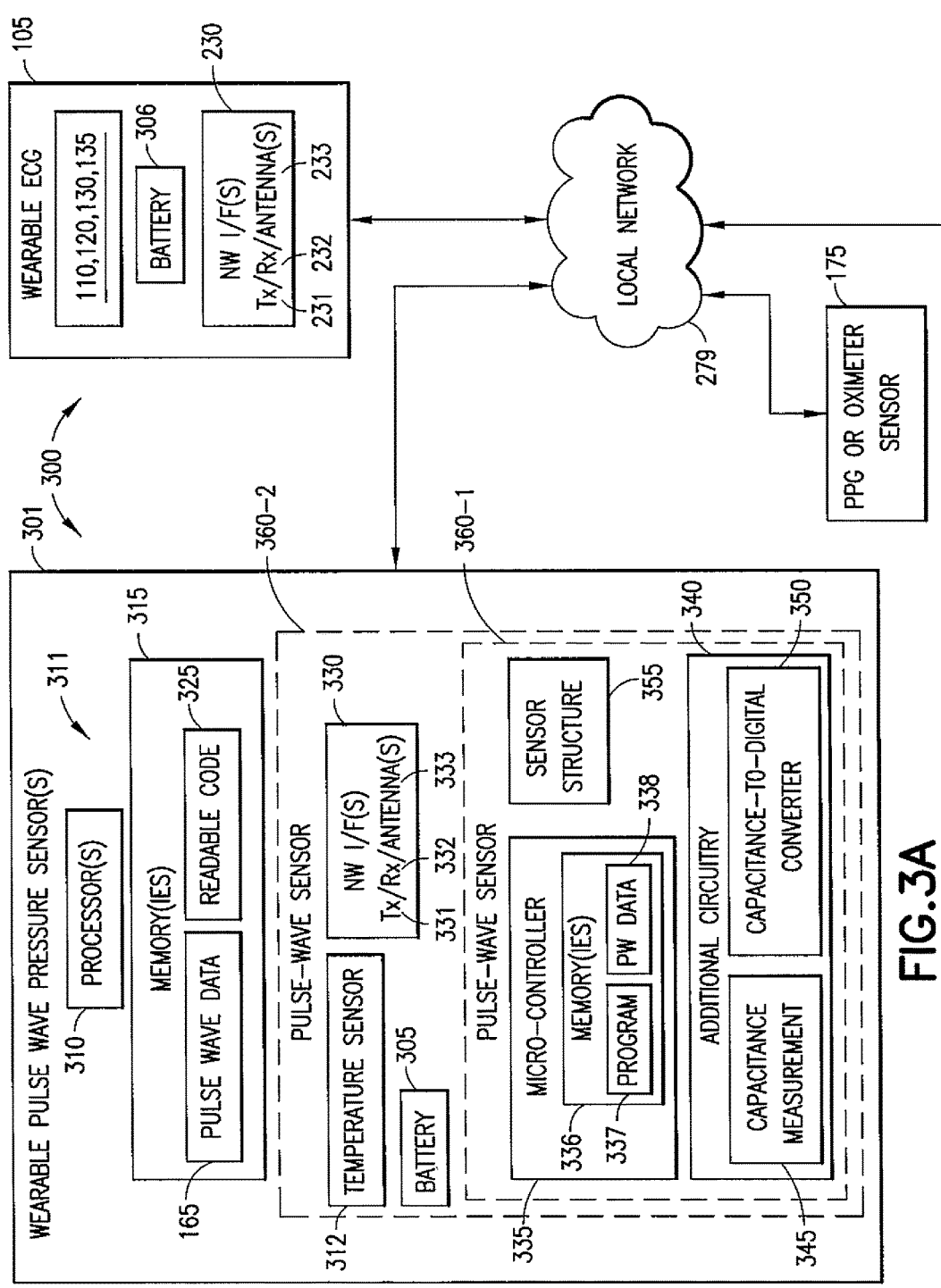
FIG. 3 is an example of a possible wearable blood pressure monitoring system interfacing with a network and server.

Referring to FIG. 3, this figure is an example of a possible wearable blood pressure monitoring system 300 interfacing with a network 379 and server 395, in accordance with certain exemplary embodiments. The system 300 comprises one or more wearable pulse wave pressure sensor(s) 301, a wearable ECG 105, and a wearable BP hub 205. Note that some embodiments may also use a pulse wave sensor such as a PPG or oximeter sensor 175, and alternatively or in addition, other embodiments may use multiple wearable pulse wave pressure sensors 301. While these are considered herein to be separate components, two or more of them may be combined. For instance, the wearable BP hub 205 and the wearable pulse wave pressure sensor 301 could be formed into a watch that is placed on the wrist. Other options are also possible, including having all three devices in the same physical device (e.g., where the local network 279 could be replaced by physical electrical connections). The components 105, 205, and 301 can communicate through the local network 279, which may be a BLUETOOTH (a global wireless communication standard that connects devices together over a certain distance) or WI-FI (a technology that allows electronic devices to connect to a wireless LAN (WLAN) network), or any other networking technology that allows devices to communicate. Additionally, the wearable BP hub 205 is described as being wearable, but this may also be fixed or portable (e.g., as part of a suite of medical instruments in a hospital). Furthermore, although each of the devices 105, 205, and 301 is described as being wireless and battery-powered, one or more of them may use wirelines (e.g., via network 279) to communicate, and one or more of them may also be plugged into another source of power (such as alternating current). The system 300 in some examples interfaces with network 379 such as the Internet (or WI-FI/LAN and the Internet) and a server 395 through the wearable BP hub 205.

A wearable pulse wave pressure sensor 301 includes, in one example, one or more processor(s) 310, a battery 305, one or more network (NW) interfaces (IIF) 330, one or more memories 315, a temperature sensor 312, and a layered and multi-sectional pulse wave sensor 360-1. Each network interface 330 typically includes a transmitter (Tx) 331, a receiver (Rx) 332, and one or more antennas 333. The one or more memories include pulse wave data 165 and computer readable code 325. In an exemplary embodiment, the one or more processors 310 execute the computer readable code 325 and cause the wearable pulse wave pressure sensor 301 to perform operations as described herein. In another example, the operations are embedded into the one or more processors 310 (or other circuitry 311), e.g., as hardware elements (such as integrated circuits, programmable logic devices, or the like), and the one or more processors 310 or the other circuitry 311 performs the operations. In a further example, some combination of hardware or code may be used to implement the operations described herein. A pulse wave pressure sensor is a sensor that senses blood flow via pressure of the blood (and other parts of a person, such as skin) produced on the sensor. A pulse wave PPG sensor is a sensor that senses blood flow, typically by using green, red and/or infrared light (and other parts of a person, such as skin) produced on the sensor. A pulse wave sensor in this disclosure means either a pulse wave pressure sensor or a pulse wave PPG sensor.

The layered and multi-sectional pulse wave sensor 360-1 comprises a micro-controller 335, a sensor structure 355, and additional circuitry 340. The micro-controller 335 comprises one or more memories 336, which comprise a program 337 of computer readable code and pulse wave data 338. The additional circuitry 340 comprises capacitance measurement circuitry 345 and capacitance-to-digital converter circuitry 350. Exemplary sensor structures are described below.

The sensor structure 355 may have one or multiple sections, such as three or six sections, each section being an individual sensor unit (also called a pixel). See the examples of possible sensors in FIG. 3, 6A, 6B, 8, 9, or 10 in U.S. patent application Ser. No. 14/872,209, filed on Oct. 1, 2015, by Afzali-Ardakani et al., with applicant of International Business Machines Corporation.

The micro-controller 335 can execute code in the program 337 to cause the pulse wave sensor 360-1 to perform operations described herein, or the operations can be embedded as hardware (e.g., in the micro-controller 335 or other circuitry), or some combination of these may be used. The micro-controller 335 can cause the capacitance measurement circuitry 345 to determine waveforms, for all of the individual sensing units, capturing changes in capacitance in the sensor structure 355 caused in response to bending of layers by a pulse wave under the skin. The waveforms are converted to digital signals by the capacitance-to-digital converter 350 and stored as PW data 338 in the one or more memories 336.

The one or more processors 310 can cause the pulse wave sensor 360-1 to transfer the PW data 338 to the one or more processors 310, which then stores the data in the memory/memories 315 as pulse wave data 165. The pulse wave data 338 and 165 may be the same or could be different, depending on implementation. For instance, the pulse wave data 338 could be sent in a stream or in bursts to the processor(s) 310, and the processors 310 would then construct the pulse wave data 165 from this, and the pulse wave data 165 could contain information from multiple pulses. The one or more processors 310 can cause the wearable pulse wave pressure sensor 301, using the one or more network interfaces 330, to transmit the pulse wave data 165 to the wearable BP hub 205 via the local network 279.

In another example, the wearable device 301 does not include the one or more processors 310 or the one or more memories 315, and "only" includes the pulse wave sensor 360-2. Pulse wave sensor 360-2 includes the battery 305 and the network interface 330 and transmits the PW data 338 to the wearable BP hub 205 via the local network 279.

The wearable ECG 105 includes one or more electrodes 110, wiring 120, ECG circuitry 130, and an ECG wave data 135 (e.g., as digital data). The wearable ECG 105 also includes a battery 306, and one or more network interfaces 230, each of which typically includes a transmitter 231, receiver 232, and one or more antennas 233. The ECG circuitry 130 may comprise one or more processors and one or more memories.

The wearable BP hub 205 includes one or more processors 210, and one or more memories 215, a battery 307, a display 250, and one or more network interfaces 240, each typically comprising a transmitter 241, a receiver 242, and one or more antennas 243. The one or more memories 215 include pulse wave data 165, ECG wave data 135, computer readable code 225, height data 226, BDC 227, and BP data 255. The BP data 255 is determined using the pulse wave data 165, the ECG wave data 135, the height data 226, and the BDC data 227 as described in more detail below. In an exemplary embodiment, the one or more processors 210 execute the computer readable code 225 and cause the wearable pulse wave pressure sensor 301 to perform operations as described herein. In another example, the operations are embedded into the one or more processors 210 (or other circuitry 206), e.g., as hardware elements, and the one or more processors 210 or other circuitry 206 performs the operations. In a further example, some combination of hardware or code may be used to implement the operations described herein.

The display 250 may or may not be present, but if present, may be used to display the BP data 255, for instance. The display 250 could be LED, LCD, or any other suitable device suitable for display of information to a user. The display could also indicate that the blood pressure is too high (e.g., using a red color), too low (e.g., using a yellow color), or is in a normal range (e.g., using a green color). Other colors, blood pressure, ranges, and indications may be used.

It should be noted that the data 165 and 135 are numbered the same even though the corresponding data exists on multiple devices. This is simply for ease of exposition. The data could be the same on all of the devices or be different.

In one example, the wearable BP hub 205 determines the BP data 255 (using techniques described below), and transmits the BP data 255 to a server 395 via a wired or wireless (or both) network(s) 379 such as the Internet or the cloud. The network interface(s) 240 are typically wireless, but could be implemented via wires. The wearable BP hub 205 may also display the blood pressure and/or stiffness index (and/or potentially other elements such as a patient's height), in addition to or in lieu of transmitting the data.

The server 395 comprises one or more processors 370 and one or more memories 380, which comprise a program 375 of computer readable code. The one or more processors 370, in response to execution of the computer readable code in the program 375, cause the server to interact with the wearable BP hub 205 to receive the BP data 255 (and other data, such as stiffness index, indication(s) whether the BP is high, normal, low, or error messages, and the like). The server 395 may also send out one or more alert(s) 376, e.g., to a doctor, nurse, hospital, patient, and the like. The doctor, nurse, hospital, and/or patient can then determine a course of action for the patient, such as prescribing a medication, diet change, lifestyle modification, or other action.

Although the computer system 395 is characterized as a "server", this is only one possibility. The computer system 395 may also be "local" to the person using the system 300, such as being an app on the person's smartphone, tablet, or computer system, or on a movable cart in a hospital. In this case, the network 379 could be a local wireless (e.g., WI-FI) or wired network. The server 395 may also be part of a cognitive/cloud system that in turn may communicate with hospitals, doctors, and/or users.

The processors 210, 310, 335, and 370 and ECG circuitry 130 may be any suitable processing device for the particular environment, such as application specific integrated circuits, single or multicore processors, low power processors (e.g., as used in smartphones or tablets), general purpose processors, digital signal processors, and the like. The memories 215, 315, 336, and 380 (and any memories in the ECG circuitry 130) may be any suitable memory, such as RAM, ROM, removable memory, memories internal or external to processors, memory that retains its values without power or only retains its values with power, and the like.

Portions or all of a data collection and a compression algorithm may be carried out in the program 337 running on the microcontroller 335 making the capacitance to digital measurements. This program could be in an assembly code. This would reduce the amount of data that would need to be transmitted (e.g., wirelessly) to the wearable BP hub 205 which would in turn lower the power consumption (an advantage for battery power operation). In the simplest example, the microcontroller 335 would know enough not to transmit when no pulse is detected (e.g., not attached to the patient yet), as opposed to continually transmitting capacitance to digital results. The microcontroller 335 could place the sensor 360-1 into an off state (e.g., where no measurements are made and, e.g., no current is passed into the capacitor(s)) in response to no pulse being detected. In addition, the microcontroller 335 could cause the sensor 360-1 to perform measurements only periodically even if a pulse is detected. Additionally, a temperature sensor 312 could be included and the microcontroller could use data from the temperature sensor 312 (e.g., configured to sense temperature from the skin) to determine whether to take sensor data or not. For instance, if the temperature reading from the temperature sensor 312 does not meet some criterion (e.g., within a few degrees of normal body temperature for a human), the microcontroller could place the sensor 360-1 into an off state (e.g., where no measurements are made and, e.g., no current is passed into the capacitor(s)).

The batteries 305, 306, and 307 are used to power their respective devices. Each of these may be one or multiple batteries and may be any suitable batter for this purpose. The batteries may or may not be rechargeable, and it's also possible for the batteries to be replaced or augmented with plugged-in sources of power, such as Alternating Current.

Now that an exemplary system has been described, additional details about possible exemplary embodiments are described. In the exemplary embodiments herein, the PPG can be replaced with a pressure sensor (e.g., the sensor structure 355), which has better sensitivity and energy efficiency and is more suitable for wearable sensing devices. In another exemplary system, two or more pulse wave sensors can be employed without employing an ECG to obtain blood pressures. In this case, pulse transit time can be obtained between two pulse wave sensors worn on two different body locations (for example, one on chest and the other on wrist). Also, two new algorithms have been developed to get both systolic and diastolic blood pressures in a way that the diastolic blood pressure (DBP) is dependent on the systolic blood pressure (SBP) and that the algorithms are simplified.

An aspect of the invention includes a new algorithm for SBP, which is different from that used previously (see Fuke, et al., in 35th Annual International Conference of the IEEE EMBS, 2013) in which a person's height has not been used. The equation by Fuke, et al., is $SBP=a*\ln(1/PTT^2)+c$ where a and c are constants and $\ln(\cdot)$ means natural logarithm. However, it is important to incorporate a subject person's height into the equation since the pulse transit time is related to the length of an artery between two sensors (e.g., ECG and pulse wave sensor). The taller a person, the longer the artery from chest to wrist. The new algorithm in this invention is $SBP_{PTT}=a*\ln(h^2/PTT^2)+b$ where h is a person's height and a and b are constants which will be empirically obtained and further optimized. The PTT may be determined as illustrated in reference to FIG. 2.

The new algorithm for DBP, which is another aspect of the invention, is $DBP=c*SBP_{PTT}+d\ T_2+e$ where c, d and e are constants which are determined empirically, and $T_2$ is a time interval between the peak point 201 of a pulse wave and the baseline point 202 where the pulse wave reaches to the baseline as shown in FIG. 2 (see $T_2$ 197).

In another aspect of the invention, an algorithm has been developed in order to include a factor of an artery stiffness index so as to determine more precise blood pressures.

One exemplary algorithm is as follows. The first equation is the following:

$$SBP=SBP_{PTT}[1+\alpha \times SI_{DVP}],$$

where $SI_{DVP}$ is a stiffness index (e.g., in cm/ms), and $\alpha$ is defined empirically. The acronym DVP means digital volume pulse which is a wrist pulse pressure.

Pulse wave velocity (PWV) is also an important factor that indicates a health condition. As shown in the prior art by Gesche, et al. Eur J Appl Physiol (2011), the PWV may be calculated as follows:

$$PWV=BDC \times height/PTT,$$

where BDC is body correlation factor (e.g., a calibrating constant without units), the height (of a person) can be in cm, the PTT is pulse transit time in ms. The height multiplied by BDC corresponds to the distance from the sternal notch to the tip of the middle finger. The NT may be determined as illustrated in reference to FIG. 2.

Figure 4:
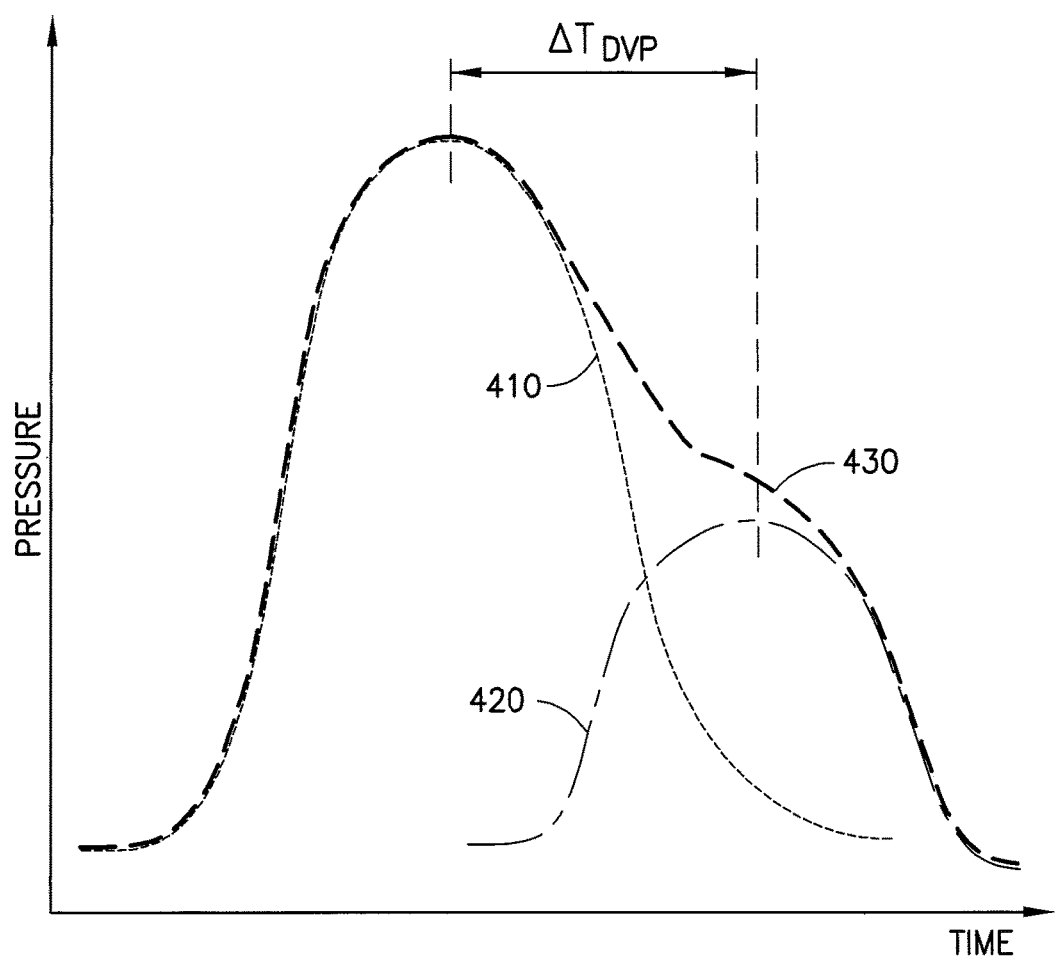
FIG. 4 illustrates a technique for determining a time difference between a forward wave point and a reflective wave point, $\Delta T_{DVP}$.

The $SI_{DVP}$ and also a $\Delta T_{DVP}$ can be determined using the wearable pulse wave pressure sensor 301. FIG. 4 illustrates a technique for determining a time difference between a forward wave point and a reflective wave point, $\Delta T_{DVP}$. The first curve 410 corresponds to the forwarding blood wave or the systolic blood pressure from heart to body, while the second curve 420 corresponds to the reflecting wave or the diastolic blood pressure while the arteries are contracting when the heart ventricle valve is closed. The units for FIG. 4 can be relative pressure/time if a pressure sensor is used or relative blood absorbance/time if a PPG is used. The third curve 430 is an envelope of the two curves 410+420. The $SI_{DVP}$ may be determined as follows:

$$SI_{DVP} = \frac{\text{Subject height}}{\Delta T_{DVP}},$$

where $SI_{DVP}$ is in cm/ms and Subject height is the height of the person being measured, in meters. Thus, the stiffness index ($SI_{DVP}$) is inversely proportional to the time difference between the forward wave point and the reflective wave point ($\Delta T_{DVP}$). It is noted that the stiffness index may be determined using pulse wave data from the wearable pulse wave pressure sensor 301, but may be determined using pulse wave data from the PPG sensor 175.

Figure 5:
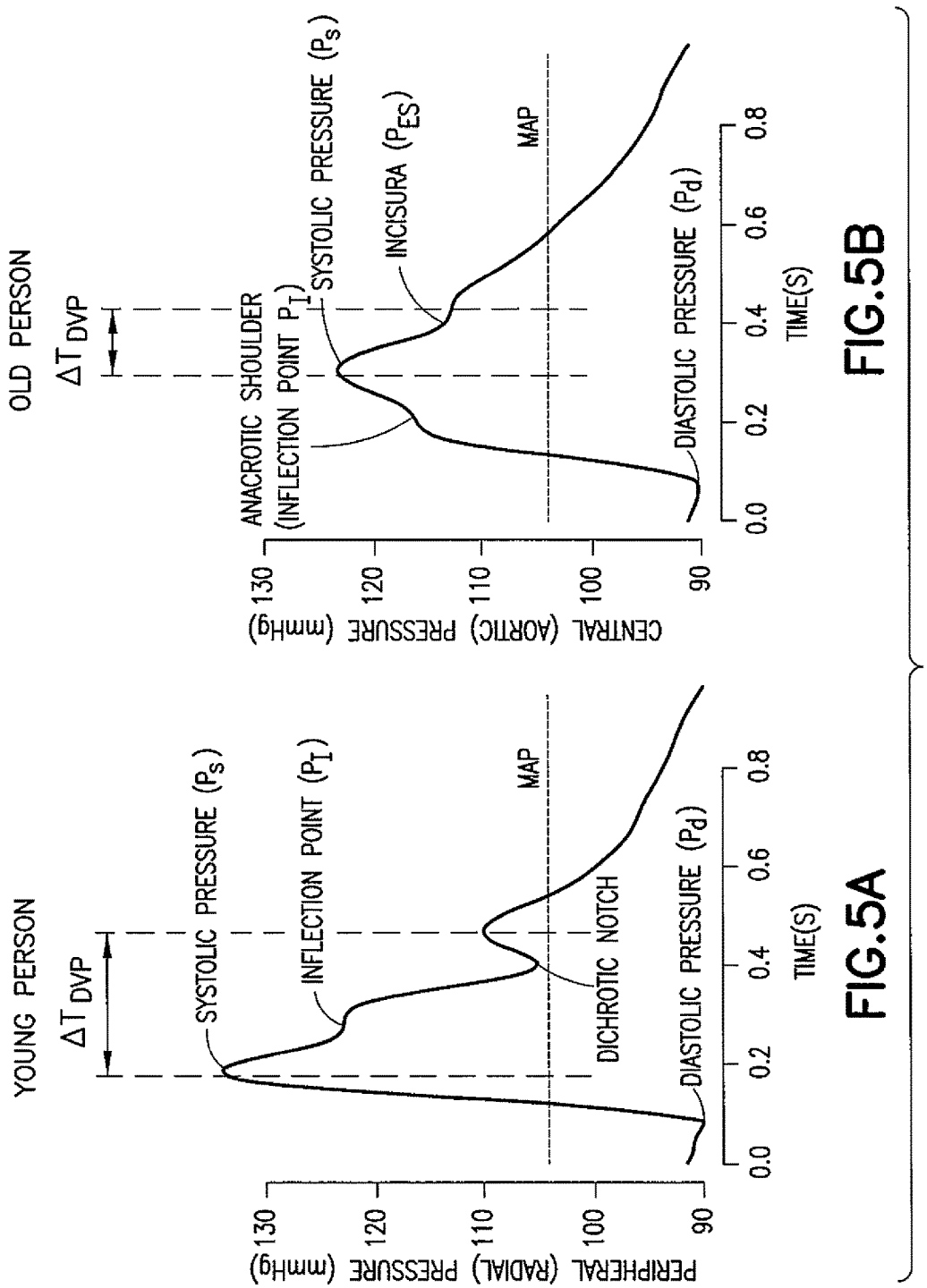
FIG. 5, which includes both

It is expected that younger persons have more flexible arteries while older persons have stiffer arteries. This is illustrated by FIG. 5, which includes both FIGS. 5A and 5B, and which illustrates the peripheral (radial) pressure in mmHg over time in seconds (s) for a young person (FIG. 5A) and an old person (FIG. 5B). As can be seen the $\Delta T_{DVP}$ is larger for the young person (see FIG. 5A), and is smaller for an old person (see FIG. 5B). Thus, the stiffness index $SI_{DVP}$ will be smaller for the young person and larger for the old person (assuming the same height for the person).

All the important health conditions discussed in this disclosure such as systolic/diastolic blood pressures, pulse transit times, stiffness indices, pulse wave velocities, forward/reflective wave points can be measured with ECG, PPG (either transmission or reflection mode), mechanical pressure sensors and/or combinations of two or more of such sensors. A reflection mode PPG sensor 175 likely can be more convenient in wearables, such as wrist watches and neck bands. All the data-collection techniques including sensor handling and algorithm-equations can also be implemented with a wide range of ECGs, PPGs, mechanical pressure sensors, and/or combinations of two or more of such sensors. Furthermore, algorithms used for these health conditions can be built into a sensor, a separate microprocessor, a smart phone and/or a personal computer, as non-limiting examples.

Figure 6:
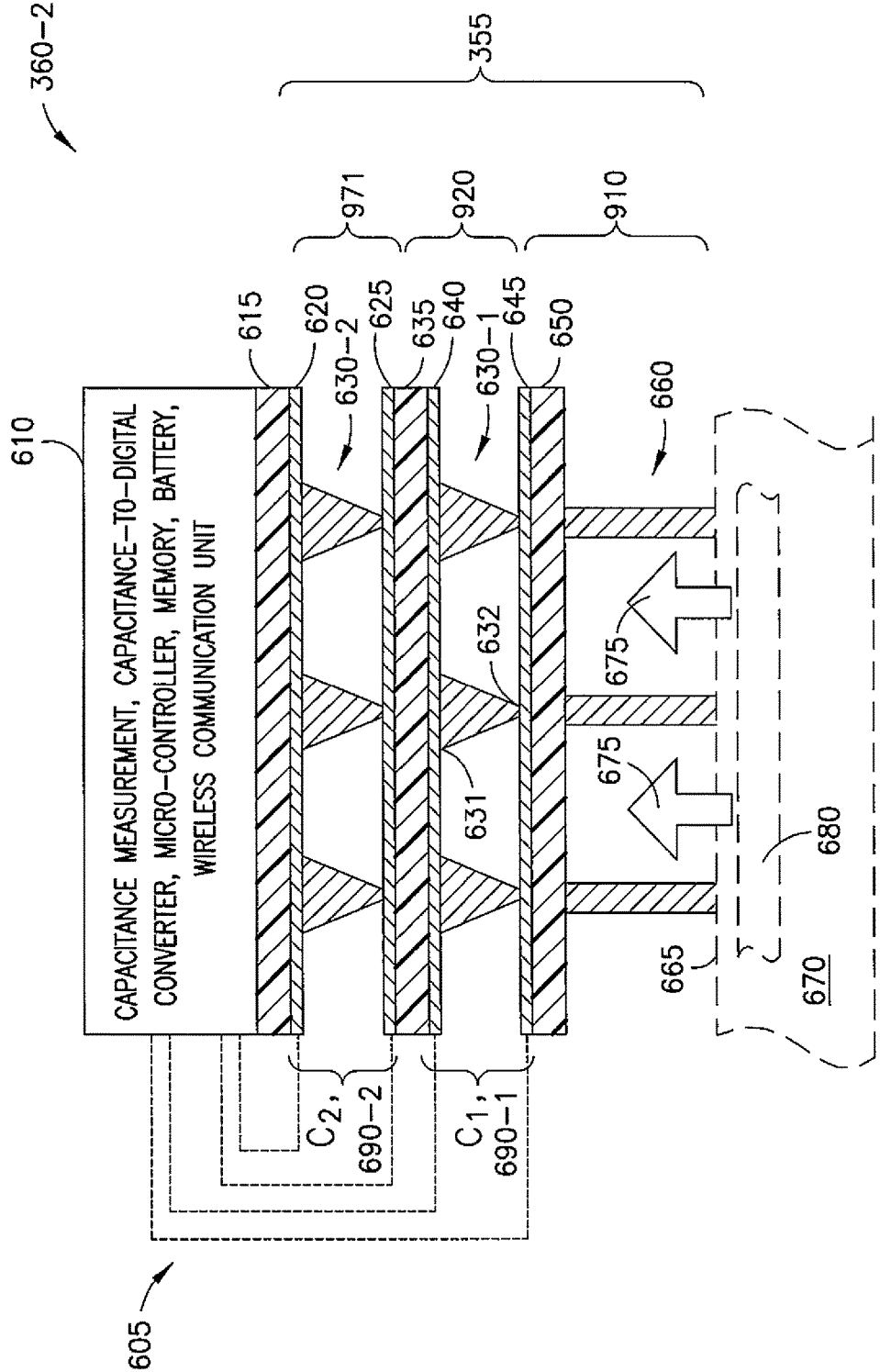
FIG. 6 illustrates a cross-section of an individual pulse wave pressure sensor of a double-layered sensor.

Possible pulse wave sensors 360 may include the following. The design of the pulse wave sensor unit, in one example, includes a dielectric layer and particularly pyramid-shaped elastomeric dielectrics to maximize the change of capacitance by the same pressure from arteries and the sensor also involves microhairs to enhance the contact of the sensor to skin so as to enhance the detection sensitivity as shown in FIG. 6. Individual pulse wave sensor unit 360-2 includes a first layer, a skin touching portion 910, and a second layer, sensing portion 920. Additionally, there is a third layer 971. The first, second and third layers form one example of a sensor structure 355. The skin touching portion 910 comprises a dielectric layer 650 and dielectric microhairs 660. The sensing portion 920 comprises conductive (e.g., metal) layers 640 and 645, and dielectric pyramids 630-1. Each dielectric pyramid 630 has a base 631 and an apex 632. The conductive layers 640 and 645 and dielectric pyramids 630-1 and air in the gap form a capacitor $C_2$, 690-1. The third sensor layer 971 comprises conductive (e.g., metal) layers 620, 625 and dielectric pyramids 630-2 and may comprise the flexible polymer layer 615. The conductive layers 620, 625 and dielectric pyramids 630-2 and air in the gap form a capacitor $C_2$, 690-2. In this example, the sensing portion 920 also includes a flexible polymer 635, although in other examples, the flexible polymer 635 may be assumed to divide the portions 910, 920. Combination of the flexible polymers 615, 635 and 650 and the thin (30 nm-300 nm) conductive layers 620, 625, 640 and 645 provides a good flexibility of the overall sensor and thus the sensor can be wearable and flexible. The individual pulse wave sensor unit 360-2 also comprises a dielectric layer 615 onto which control circuitry 610 is attached. The control circuitry 610 includes, in this example, capacitance measurement circuitry, capacitance-to-digital converter circuitry, a micro-controller, a memory (e.g., to store a program for the micro-controller and to store digitized pulse wave(s)), a battery, and a wireless communication unit. Control circuitry 610 typically includes the elements 305, 330, 335, 340, and 336 from FIG. 3, and also may include the temperature sensor 312. Note that one or both of the capacitance measurement circuitry and/or the capacitance-to-digital converter may be implemented by the micro-controller 335. Additionally, the control circuitry 610 may use AC (alternating current) or other power source instead of or in addition to a battery. The various conductive layers 620, 625, 640, and 645 may be interconnected via the connectors 605 and the control circuitry 610. The connectors 605 may be wires, metal runs on a circuit board or integrated circuit, and the like.

In this example, the individual sensor unit 360-2 is shown contacting skin 665 of a body part 670, which contains one or more arteries 680 (of which one is shown in FIG. 6). The arteries 680 generate pulse pressures 675 that pass through the first and second portions 910, 920 (and the third sensor layer 971) and cause squeezing (e.g., deformation and bending) of the elastomeric pyramids 630 of the first and second portions 910, 920 (and the third layer 971) at least to some extent. This squeezing therefore causes a capacitance change, and the circuitry 610 can determine waveforms capturing this change. Additionally, the first and second portions 910, 920 (and the third layer 971) are configured to create a capacitance change in response to a return of the portions to an original state with a release of the pulse pressure. It is assumed that at least the elements 615 and 620 are fixed (e.g., to a watch for instance) and the squeezing occurs between the elements 615/620 and the portions 910, 920, and part (e.g., elements 625, 630) of 971. It is desirable that the squeezing occurs mostly with the elastomeric pyramids so that the change of the capacitance between the two conductive layers 645 and 640 or 625 and 620 can be maximized.

The shape of the dielectrics 630-1, 630-2 are exemplary, but use of pyramid shapes helps to increase the pulse wave signal to noise ratio so as to improve the data quality. The dielectric pyramids 630-1, 630-2 may be made of polymeric elastomer such as polydimethylsiloxane (PDMS). The two capacitors $C_1$, 690-1 and $C_2$, 690-2 are operated in series in an embodiment.

Figure 7:
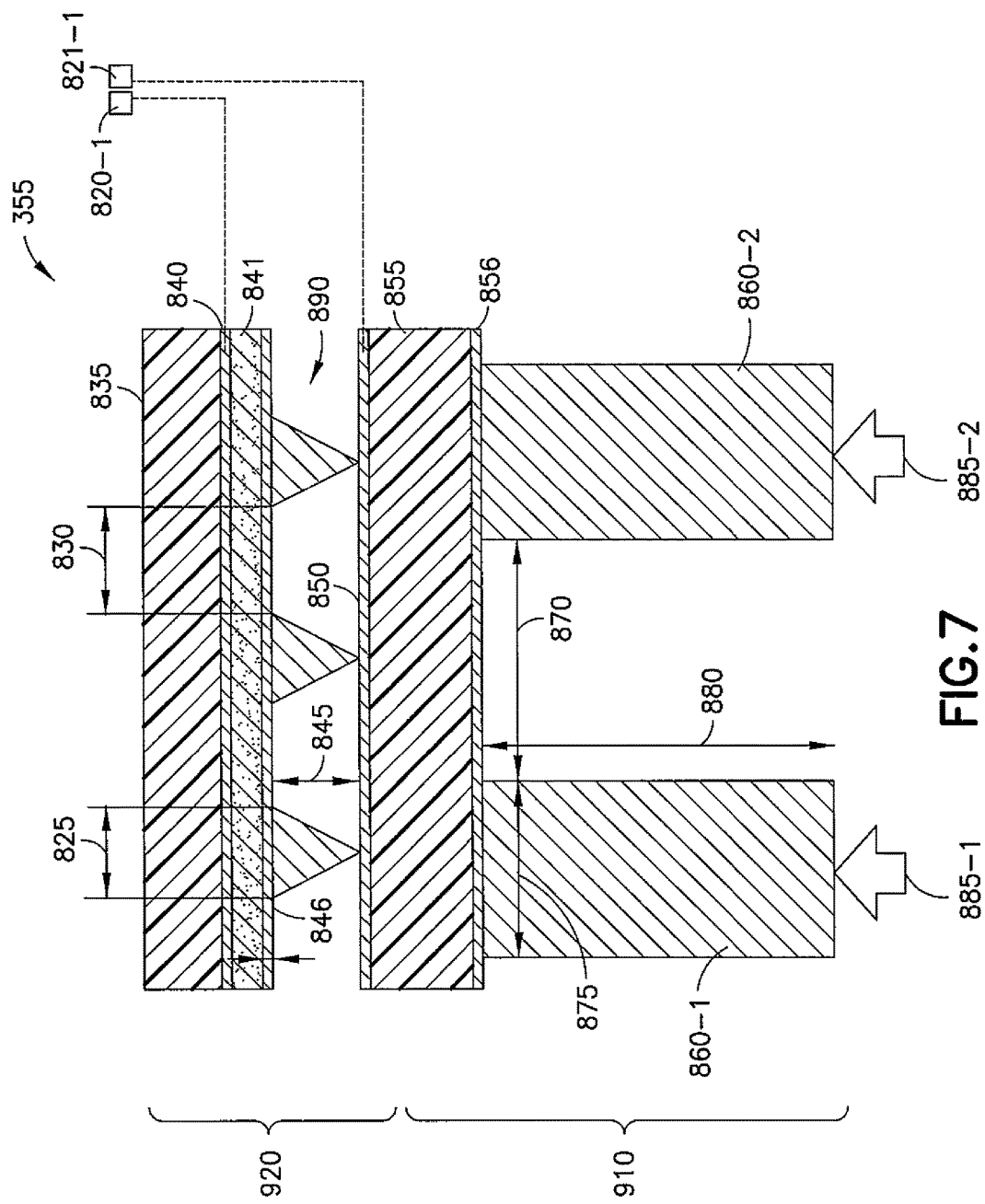
FIG. 7 is a cross section of a possible example of a layered and multi-sectional pulse wave pressure sensor structure.

Referring to FIG. 7, FIG. 7 is a possible example of a sensor structure 355 used as a pulse wave sensor. FIG. 6 and other previous figures are also referred to for the description of FIG. 7. In this example, the sensor structure 355 includes a polymer film 835 (e.g., a dielectric 635), a Cr/Au/Cr layer 840 (e.g., conductive layer 640), an adhesive layer 841, PDMS pyramids 890 (e.g., dielectric pyramids 630-1), a Cr/Au layer 850 (e.g., conductive layer 645), a polymer film 855 (e.g., a dielectric 650), an adhesive layer 856, and PDMS microhairs 860-1 and 860-2. The sensor structure 355 has output contacts 820-1 and 821-1, which would be connected to the capacitance measurement 345. The conductive layer 840 comprises Cr/Au/Cr. Cr promotes the adhesion to the polymer film 835 and to the adhesive layer 841. Instead of Cr other metals such as Ti and TiW can be used. The wiring pads 820-1 and 821-1 have only Cr/Au as the surface of Au is bonded to another metal for electrical connection. The PDMS microhairs 860-1 and 860-2 are operated on by the pulse pressures 885-1 and 885-2, respectively. This causes a corresponding squeezing of the portion 910 and part of 920 (e.g., the layer 850 and pyramids 890), as the film 835 is assumed to be fixed, e.g., to a watch or neckband or other wearable, and there is a corresponding capacitance change. Additionally, there is a capacitance change in response to a return of the portion 910 (e.g., and part of portion 920) to an original state. In this example, the pyramid base's width 825 is 10 μm, the distance 830 between edges of pyramids is 20 μm, distance 845 between a surface of a thin layer 846 of PDMS and a surface of the Cr/Au layer 850 is 7-8 μm, distance 870 between the PDMS microhairs 860 is 60-120 μm, hair length 880 of the PDMS microhairs 860 is 150-450 μm, and diameter 875 (e.g., assuming the microhairs are cylindrical) of the PDMS microhairs 860 is 20-50 μm. The adhesive layers can be made from a Phenoxy resin with a low molecular weight. See the InChem Corp online brochure on www.phenoxy.com. Furthermore, the elastomeric polymer (e.g., as used in the pyramids 890) may comprise polydimethylsiloxane, the flexible polymer film (e.g., as used in the polymer film 855) may comprise polyester, polyimide, polyethylene, polypropylene, polycarbonate, polyvinyl chloride, acrylic polymer, fluorinated polymer, polyethylene naphthalene or combination of two or more of these polymers, and the adhesive may comprise Phenoxy resins or polyvinyl alcohol.

Figure 8:
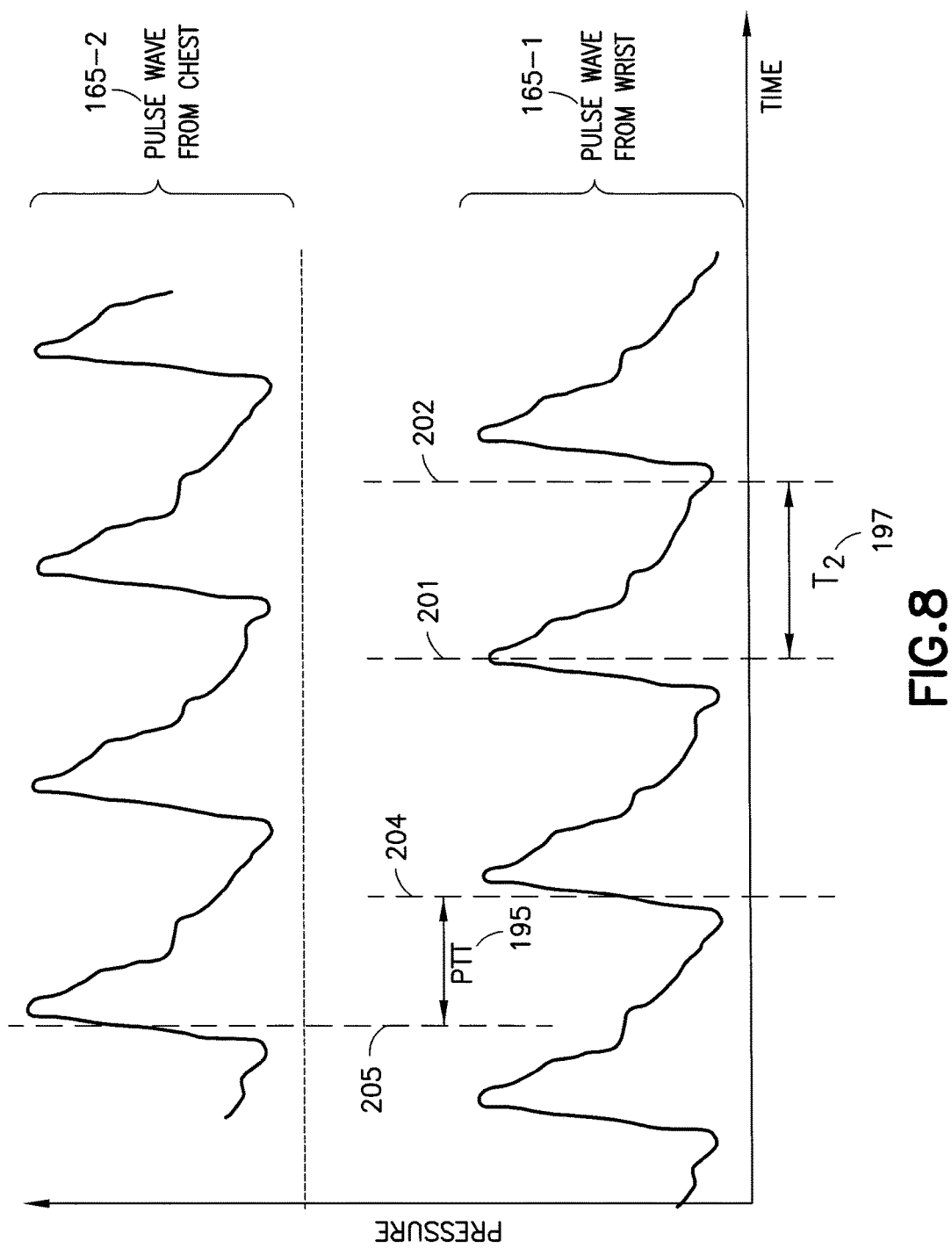
FIG. 8. is a graph on the same time scale of two different pulse waves, and illustrates determination of pulse transit time (PTT) between heart and wrist and time difference between a forward wave point and the ending point of the wave ($T_2$).

In terms of the examples herein, it has been primarily assumed that one wave from an ECG would be used and one pulse wave from a pulse wave pressure sensor would also be used, where the pulse wave pressure sensor was usually on the wrist. However, it is possible to determine the PTT and other information using two pulse wave sensors and the data from them. Turning to FIG. 8, this figure is a graph on the same time scale of two different pulse waves, and illustrates determination of pulse transit time (PTT) between heart and wrist and time difference between a forward wave point and the ending point of the wave ($T_2$). This particular example uses radial artery pulse wave data 165-1, which is pulse wave data from the wrist. Also, another pulse wave 165-2 is shown, this one from the chest. The pulse transit time (PTT) 195 may be determined by comparing the maximum inclination 205 of the chest pulse wave data 165-2 and the corresponding maximum inclination 204 of the radial artery pulse wave data 165-1. The $T_2$ 197 is described above.

In this example, one of the pulse waves 165-1/165-2 is determined using a pulse wave pressure sensor such as shown in FIG. 6 or 7, or a PPG. The other pulse wave 165-1/165-2 may be determined using another pulse wave pressure sensor such as shown in FIG. 6 or 7, or a PPG or oximeter sensor 175. The locations of the pulse waves from the chest or a neck or an arm close to the chest and the wrist or the finger are also merely exemplary.

The following are additional examples.

A system with ECG, pulse wave sensors, and electronic hub can diagnose various cardiovascular diseases that include but are not limited to high blood pressure, hypertension, arrhythmias, pulse rates, sinus blocks, and pacemaker impulse. A system with ECG, pulse wave sensors, and additional sensors such as a sound sensor, a strain gauge sensor, and/or an electromyography (EMG) sensor can act to provide more data with integration to the electronic hub in support of continuous or timed or periodic measurements and correlation with the heart, blood flow and/or blood pressure as well as other data that could aide modeling and analytical characterization of the body.

Further, it is possible to use a controlled manual, semi-automated or automated blood pressure wrist, arm, or other location blood pressure monitor which can provide a secure position to begin an inflation step of a bladder or cuff such that blood flow is altered or stopped for a short time, followed by bladder pressure relief while sensors characterize the blood pressure and/or blood flow. Such a periodic measurement or measurements can aide in blood pressure calibration under controlled measurement conditions such as having a person or patient remain relatively still during this procedure. This may be performed in a doctor's office, for instance.

Further calibration of the relative stiffness of arteries and veins may be determined via measurement of the pulse wave of blood flow with multiple sensors such as those highlighted above and with blood pressure measurements due to a periodic, inflatable bladder to restrict blood flow with increased pressure and measurement at elevated bladder pressure down through reduced or no bladder pressure while monitoring blood flow, relative pulse shape and/or blood pressure. Ultrasound characterization between sensors may also be deployed to determine distance between sensor on a person or other animals.

The system can incorporate encryption in system hardware, communications and use to provide security on personal information, tracking, recording and access.

Use of one or more electrical contacts ECG and/or EMG sensors may improve quality of data. The one or more sensors may be on the body as a wearable device adhesively joined in a temporary manor to the skin or may be joined to or be part of clothing or other wearable solutions.

The pulse wave sensors may be on the body such as on the chest cavity or elsewhere as a wearable such as by using an adhesive to form a temporary attachment to the skin, integrated into a shirt or attached to a shirt, pants, socks or other clothing, in a watch band or ankle bracelet. The use of two or more sensors may take advantage of ultrasound sensors or sound communication to provide reference of distance from one sensor to another. For instance, when measuring the pulse transit time using an ECG and a pulse wave sensor, there can be an error due to the difference between the heart's electrical R signal and the heart's ventricle valve opening as the ventricle muscle squeezes blood to make the valve open. The error can be limited if two pulse wave sensors instead of one ECG and one pulse wave sensor are used. However, it is not easy to employ the two pulse wave sensors due to signal detection issues.

One or more ECG and/or EMG sensors may be co-located in close proximity with one or more pulse wave sensors such as at or near the heart, on the chest cavity, an arm(s), leg(s) or elsewhere on the body. One or more ECG and/or EMG sensors may be used, which are located remotely from the pulse wave sensor or sensors such as but not limited to on the torso/chest cavity for ECG and or EMG and on legs and/or arms for pulse wave sensor(s). Data from ECG/EMG and pulse wave sensors can be communicated between sensors and such data collection may be performed by, e.g., a microprocessor by wired communication, wireless communication or both.

The blood pressure monitoring systems described above may be used with other sensors such as motion sensors, accelerometers, gyroscopic sensors, temperature sensors, humidity sensors, oxygen sensors, chemical sensors, and the like. These sensors may be used on the body for client evaluation in at least the following scenarios: while resting (e.g., sleeping), lying down, sitting up, standing, as examples; while exercising or moving such as walking, running, swimming; while under stress such as at work, having a lack of sleep, and/or being in dangerous environment; and relative to the environment, temperature, humidity, sea level high altitude, low oxygen, polluted air environment, chemical exposure and other environmental conditions.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium does not include a propagating wave.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the designer's computer, partly on the designer's computer, as a stand-alone software package, partly on the designer's computer and partly on a remote computer or entirely on the remote computer or server. In the latter scenario, the remote computer may be connected to the designer's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The following abbreviations that may be found in the specification and/or the drawing figures are defined as follows:
BDC body correlation factor
BP blood pressure
cm/ms centimeters per millisecond
CVD cardiovascular disease
DVP digital volume pulse
DBP diastolic blood pressure
EKG or ECG electrocardiogram
EMG electromyography
I/F interface
LAN local area network
LCD liquid crystal display
LED light emitting diode
mmHg millimeters of mercury
m/s meters per second
NW network
PPG photoplethysmography or photoplethysmogram
PTT pulse transit time
PWV pulse wave velocity
Rx receiver
SBP systolic blood pressure
SI stiffness index (e.g., in cm/ms)
Tx transmitter
WLAN wireless local area network

What is claimed is:
1. An apparatus comprising:
at least one pulse wave pressure sensor where pulse wave data is received from, wherein receiving of the pulse wave data is via one of a wireless or wired interface, wherein the at least one pulse wave pressure sensor comprises a layered structure configured, in response to pulse waves in a person, to generate electronic pulse waves in a form of a capacitance versus time;

an electrocardiogram sensor where electrocardiogram data is received from, wherein the receiving of the electrocardiogram data is via one of a wireless or wired interface; and one or more memories storing computer readable code; and one or more processors, wherein the one or more processors, in response to loading and executing the computer readable code, cause the apparatus to perform operations comprising:

receiving electrocardiogram data comprising data from the electrocardiogram sensor;

receiving pulse wave data from the at least one pulse wave pressure sensor, the pulse wave data comprising data from one or more pulse waves from the person;

determining blood pressure using at least the electrocardiogram data and the pulse wave data; and outputting an indication of the blood pressure.

2. The apparatus of claim 1, wherein the at least one pulse wave pressure sensor further comprises:

a sensor structure, comprising:

a first portion configured to contact the person at a skin surface of the person where the sensor structure is capable of taking readings concerning arteries or veins or both thereunder;

a second portion that contacts the first portion and is configured to have a capacitance, wherein a pulse pressure under the skin causes squeezing or bending between the first portion and a fixed part of the second portion, and wherein the first and second portions are configured to create a capacitance change in response to the squeezing or bending caused by the pulse pressure in relation to a return to an original state of the first portion with a release of the pulse pressure; and circuitry connected to the sensor structure and configured to measure and transmit a waveform for the sensor structure and configured to digitize the measured waveform, wherein the waveform captures the capacitance change.

3. The apparatus of claim 1, wherein determining blood pressure using at least the electrocardiogram data and the pulse wave data further comprises determining a systolic blood pressure based on pulse transit time (PTT) ($SBP_{PTT}$) using the following:

$$SBP_{PTT}=a*\ln(h^2/PTT^2)+b,$$

where h is the person's height, a and b are constants which are empirically obtained, PTT is a pulse transit time determined using the electrocardiogram data and the pulse wave data, and ln(•) means natural logarithm, and wherein PTT is determined as a time between an R peak in the electrocardiogram data and a corresponding maximum inclination in pulse wave data from the at least one pulse wave pressure sensor.

4. The apparatus of claim 3, wherein the one or more processors, in response to loading and executing the computer readable code, further cause the apparatus to perform operations comprising:

outputting an indication of the systolic blood pressure based on pulse transit time (PTT) ($SBP_{PTT}$), wherein the outputting is to one or more of a display or a wireless or wired network interface.

5. The apparatus of claim 3, further comprising one or more photoplethysmography sensors.

6. The apparatus of claim 5, wherein at least one of the one or more photoplethysmography sensors comprises a reflection-mode photoplethysmography sensor.

7. The apparatus of claim 3, wherein determining blood pressure using at least the electrocardiogram data and the pulse wave data further comprises determining diastolic blood pressure using the following:

$$DBP=c*SBP_{PTT}+dT_2+e,$$

where c, d and e are constants which are empirically obtained, and $T_2$ is determined using the pulse wave data from the at least one pulse wave pressure sensor and is a time interval between a peak point of a pulse wave and a baseline point where the pulse wave reaches to the baseline.

8. The apparatus of claim 7, wherein the one or more processors, in response to loading and executing the computer readable code, further cause the apparatus to perform operations comprising: outputting one or more indications of one or more of the following:

the systolic blood pressure based on pulse transit time (PTT) ($SBP_{PTT}$) and the diastolic blood pressure, wherein the outputting is to one or more of a display or a wireless or wired interface.

9. The apparatus of claim 7, further comprising a photoplethysmography sensor.

10. The apparatus of claim 9, wherein photoplethysmography sensor comprises a reflection-mode photoplethysmography sensor.

11. The apparatus of claim 7, wherein determining blood pressure using at least the electrocardiogram data and the pulse wave sensor data further comprises:

determining the systolic blood pressure using the following equation:

$$SBP=SBP_{PTT}[1+\alpha \times SI_{DVP}],$$

where SBP is systolic blood pressure, $SBP_{PTT}$ is the systolic blood pressure based on the pulse transit time (PTT), $\alpha$ is defined empirically, and $SI_{DVP}$ is a stiffness index determined using the pulse wave data.

12. The apparatus of claim 11, wherein the one or more processors, in response to loading and executing the computer readable code, further cause the apparatus to perform operations comprising:

outputting one or more indications of one or more of the following:

the systolic blood pressure based on pulse transit time (PTT) ($SBP_{PTT}$), diastolic blood pressure, and the systolic blood pressure, wherein the outputting is to one or more of a display or a wireless or wired network interface.

13. The apparatus of claim 11, wherein the pulse wave data used for determination of the stiffness index is from a photoplethysmography sensor.

14. The apparatus of claim 13, where the photoplethysmography sensor comprises a reflection-mode photoplethysmography sensor.

15. The apparatus of claim 11, wherein the stiffness index $SI_{DVP}$ is determined using the following:

$$SI_{DVP} = \frac{\text{height}}{\Delta T_{DVP}},$$

where height is the height of the person and $\Delta T_{DVP}$ is a time difference between a forward wave point and a reflective wave point and is determined using the pulse wave data.

16. The apparatus of claim 15, further comprising a photoplethysmography sensor, and wherein the pulse wave data used for determination of the stiffness index is from the photoplethysmography sensor.

17. The apparatus of claim 16, where the photoplethysmography sensor comprises a reflection-mode photoplethysmography sensor.

18. The apparatus of claim 15, wherein the one or more processors, in response to loading and executing the computer readable code, further cause the apparatus to perform operations comprising:
outputting one or more indications of one or more of the following:
the systolic blood pressure based on pulse transit time (PTT) ($SBP_{PTT}$),
diastolic blood pressure,
the systolic blood pressure, and
the stiffness index,
wherein the outputting is to one or more of a display or a wireless or wired network interface.

19. An apparatus comprising:
an electrocardiogram sensor configured to receive electrocardiogram data, the electrocardiogram data comprising data from an electrocardiogram from a person;
at least one pulse wave pressure sensor configured to receive pulse wave data from one or more pulse waves of the person;
one or more memories storing computer readable code; and
one or more processors, wherein the one or more processors, in response to loading and executing the computer readable code, are configured to cause the apparatus to perform operations comprising:
determining blood pressure, comprising: determining a systolic blood pressure based on pulse transit time ($SBP_{PTT}$) using the following:

$$SBP_{PTT}=a*\ln(h^2/PTT^2)+b,$$

where h is the person's height, a and b are constants which are empirically obtained, PTT is a pulse transit time determined using the electrocardiogram data and the pulse wave data, and ln( ) means natural logarithm, and wherein PTT is determined as a time between an R peak in the electrocardiogram data and a corresponding maximum inclination in the pulse wave data, and
outputting an indication of the determined blood pressure.

20. The apparatus of claim 19, wherein the at least one pulse wave pressure sensor comprises a layered structure configured, in response to pulse waves in the person, to generate electronic pulse waves in a form of a capacitance versus time.

21. The apparatus of claim 19, wherein the at least one pulse wave pressure sensor further comprises:
a sensor structure, comprising:
a first portion configured to contact the person at a skin surface of the person where the sensor structure is capable of taking readings concerning arteries or veins or both thereunder;
a second portion that contacts the first portion and is configured to have a capacitance, wherein a pulse pressure under the skin causes squeezing or bending between the first portion and a fixed part of the second portion, and
wherein the first and second portions are configured to create a capacitance change in response to the squeezing or bending caused by the pulse pressure in relation to a return to an original state of the first portion with a release of the pulse pressure; and
circuitry connected to the sensor structure and configured to measure and transmit a waveform for the sensor structure and configured to digitize the measured waveform, wherein the waveform captures the capacitance change.

22. The apparatus of claim 19, wherein determining blood pressure further comprises determining diastolic blood pressure using the following:

$$DBP=c*SBP_{PTT}+dT_2+e,$$

where c, d and e are constants which are empirically obtained, and $T_2$ is determined using the pulse wave data from the at least one pulse wave pressure sensor and is a time interval between a peak point of a pulse wave in the pulse wave data and a baseline point where the pulse wave reaches to the baseline.

* * * * *